(12) United States Patent
Linnane et al.

(10) Patent No.: US 8,075,507 B2
(45) Date of Patent: Dec. 13, 2011

(54) RELATING TO SOCKS

(75) Inventors: Patrick G. Linnane, Elsmere Port (GB); Paul Hanmer, Chester (GB); David G. Wild, Wirral (GB); Duncan J. Rowley, Wirral (GB); Ian S. Tabron, Cheshire (GB); Wayne L. Bonnefin, Chester (GB); Simon M. Adams, Flintshire (GB)

(73) Assignee: ConvTec Technologies Inc., Las Vegas, NV (US)

(*) Notice: Subject to any disclaimer, the term of this patent is extended or adjusted under 35 U.S.C. 154(b) by 340 days.

(21) Appl. No.: 11/945,666

(22) Filed: Nov. 27, 2007

(65) Prior Publication Data
US 2008/0071204 A1    Mar. 20, 2008

Related U.S. Application Data

(62) Division of application No. 11/093,407, filed on Mar. 30, 2005, now abandoned.

(30) Foreign Application Priority Data

Mar. 31, 2004 (GB) .................................. 0707371.4

(51) Int. Cl.
*A61F 5/00* (2006.01)

(52) U.S. Cl. ........................................................ 602/23

(58) Field of Classification Search ............... 602/30, 602/60–63, 75, 23, 27; 2/239–241; 66/172 E, 66/182, 185
See application file for complete search history.

(56) References Cited

U.S. PATENT DOCUMENTS

| 3,605,122 | A  |   | 9/1971  | Myers |
| 4,373,361 | A  | * | 2/1983  | Thorneburg ............ 66/178 R |
| 4,732,015 | A  |   | 3/1988  | Abrams |
| 5,555,565 | A  | * | 9/1996  | Gallagher, Jr. ............... 2/239 |
| 6,158,253 | A  |   | 12/2000 | Svoboda |
| 6,173,452 | B1 |   | 1/2001  | Kelly |
| 6,286,151 | B1 |   | 9/2001  | Lambertz |
| 6,308,337 | B1 |   | 10/2001 | Penley |
| 6,341,505 | B1 |   | 1/2002  | Dahlgren |
| 2004/0111048 | A1 | * | 6/2004 | Jensen et al. ............... 602/13 |

FOREIGN PATENT DOCUMENTS

| DE | 20307702 | 8/2003 |
| DE | 20318854 | 3/2004 |
| EP | 1076540 | 2/2001 |
| FR | 2662602 | 12/1991 |
| GB | 2337444 | 11/1999 |
| WO | WO03056084 | 7/2003 |

* cited by examiner

*Primary Examiner* — Michael A. Brown
(74) *Attorney, Agent, or Firm* — John M. Kilcoyne

(57) ABSTRACT

A sock suitable for wearing on a limb of a patient, the sock comprising material having the ability to wick moisture away from the skin surface and the sock comprising padding located in those areas of the sock which in use will cover the ankle and shin of the patient.

5 Claims, 3 Drawing Sheets

RELATING TO SOCKS

FIELD OF THE INVENTION

The present invention relates to a sock suitable for wearing on a limb and particularly to a sock for use on the leg. The sock is particularly suited for use with a compression device for the limb and in the type of compression therapy used in the treatment of venous leg ulcers, deep vein thrombosis (DVT), vascular disorders and the reduction of oedema. The invention further relates to a pair of such socks, and to a kit comprising such a sock.

BACKGROUND OF THE INVENTION

Ulceration of the lower limbs affects a significant proportion of the population over the age of sixty. Although there are several forms of ulcer one of the more common is the venous leg ulcer, which is believed to result from failure of the valves within the venous system. The failure of these valves reduces the efficiency of return of blood from the limb and this is believed to correlate to the incidence of ulceration.

Venous leg ulcers are currently treated both by the use of a dressing to the wound and the application of compression to the affected limb. Compression is conventionally applied by either the use of bandages or stockings, with the tension within the fabric structure of these products generating compressive force. The effectiveness of the dressings, which allow the passage of water vapor from the wound, is impaired by the application of conventional compression materials, particularly bandages. Some of the wound exudates can leak around or through the dressing, creating wetness; this fluid contains enzymes that can cause maceration of the surrounding skin which is of course undesirable.

Bandages or stockings are furthermore uncomfortable to wear, especially in hot weather, as moisture cannot easily escape. With bandages and stockings, the bony prominences, such as the shin bone and ankle bone, receive concentrated pressure levels and therefore an under layer of soft non woven padding is also used, to pad the limb and make its cross section more circular.

This padding may also perform the function of absorbing any fluid that escapes from the dressing. However, it is a skilful and difficult to perfect job to locate the padding appropriately, and the bandages may subsequently move and dislodge the padding.

Compression may also be applied using a constrained air bladder, which solves some of the problems associated with the use of bandages and stockings. The air bladder itself is impermeable to vapor and this can therefore cause problems, as heat and moisture from sweat are trapped by the bladder.

Accordingly, there is a need for means for alleviating the problems associated with the use of known compression systems for leg ulcer patients.

SUMMARY OF THE INVENTION

The present invention provides, in a first aspect, a sock suitable for wearing on a limb of a leg ulcer patient, the sock comprising material having the ability to wick moisture away from the skin surface.

Some, most, substantially all, or all of the ankle portion of the sock may comprise material having the ability to wick moisture away from the skin surface. Preferably, all of the area, or substantially all of the area, that, in use, will be coextensive with the patient's ankle comprises material having the ability to wick moisture away from the skin surface.

All, or substantially all, of the gaiter region of the sock may comprise material having the ability to wick moisture away from the skin surface.

Preferably, the sock comprises material having the ability to wick moisture away from the skin surface in all regions.

Such a sock is advantageous as it can be worn on a leg of a leg ulcer patient, over a dressing to the wound, whilst not impairing the effectiveness of the dressing, which allows the passage of water vapor from the wound.

Accordingly, the wearing of the sock can assist in maintaining healthy skin in the region of the ulcer. The sock is particularly effective for use by leg ulcer patients having leg ulcers in the gaiter region, which is the area in which it is most common for leg ulcers to occur.

The material having the ability to wick moisture away from the skin surface may be any material with moisture wicking properties. In particular, the material may be fibers having the ability to wick. The fibers may suitably be knitted into the sock or the sock may be knitted from a wicking fiber or from a combination of two or more different fibers including one or more wicking fibers. Suitable wicking fibers include Coolmax™, Duraspun™, Isolfil™, polypropylene, polyester microfiber and Soft Touch™ P180W and Galaxy™ or other fibers with a large surface area.

When fibers other than wicking fibers are included, these may be any fibers suitable for use in a sock and may be natural fibers or synthetic fibers or a combination thereof. Preferably the sock comprises a blend of cotton and Coolmax Antibacterial™ fibers or a blend of cotton and polypropylene. The blend may comprise from 5% to 80% by weight of wicking fibers; and preferably from 20% to 60% by weight of wicking fibers; and more preferably from 25% to 50% by weight of wicking fibers blended with natural or synthetic fibers suitable for use in a sock.

Wicking is the transport of fluid within a yarn or fabric structure. This process is governed by the arrangement of the fibers comprising the structure and by the ease with which the fluid wets out the fiber surface.

Preferably, the sock is knitted with a stitch pattern that encourages moisture transfer to other areas of the sock. Useful stitches/processes for producing useful stitches include rib, rib loop transfer, pelerine plain loop transfer, single or double jersey and jacquard double jersey.

In particular, stitch patterns that encourage moisture transfer to areas of the sock that, in use, will not be covered by the patient's footwear or a compression sleeve are preferred. More preferably, stitch patterns that encourage moisture transfer to areas of the sock that, in use, will not be covered by the patient's footwear or by any compression applying means, such as bandages, compression stockings, compression sleeves or air bladders, being worn, may be used.

Preferably, the material having the ability to wick moisture away from the skin surface includes one or more wicking fibers on the side of the material that in use is on the inner surface of the sock, adjacent the skin, and includes absorbent material, such as absorptive fibers, on the side that in use is on the outer surface of the sock. For example, the material having the ability to wick moisture away from the skin surface may be a wicking fiber, or from a combination of two or more different fibers including one or more wicking fibers, located on the side that in use is on the inner surface of the sock, whilst it may be knitted from an absorptive fiber, or from a combination of two or more different fibers including one or more absorptive fibers, on the side that in use is on the outer surface of the sock. Thus, an aim of the wicking fibers is, in many embodiments, to transport moisture to the outside of the sock.

When the sock is used in combination with a compression sleeve an aim of the wicking fibers is to transport moisture to those areas of the sock not covered by the compression sleeve or to those areas from which evaporation of moisture is possible.

The sock may suitably further comprise ventilation channels running away from the ankle portion, along which water vapor may be transferred laterally, for example by diffusion and/or by air flow, currents or convention. The ventilation channels may suitably be of a ribbed construction. The sock may comprise a foot portion that includes ventilation channels running away from the ankle portion, along which water vapor may be transferred laterally, for example, by diffusion and/or by air flow, currents or convention.

The sock may alternatively or additionally comprise a leg portion that includes ventilation channels running away from the ankle portion, along which water vapor may be transferred laterally, for example, by diffusion and/or by air flow, currents or convention.

The sock preferably further comprises a leg portion including an area made from material having the ability to wick moisture away from the skin surface. The material having the ability to wick moisture away from the skin surface may be as described above in relation to the ankle portion and may be the same as or different to the material having the ability to wick moisture away from the skin surface used in the ankle portion.

The sock preferably further comprises a foot portion including an area made from material having the ability to wick moisture away from the skin surface. The material having the ability to wick moisture away from the skin surface may be as described above in relation to the ankle portion and may be the same as or different to the material having the ability to wick moisture away from the skin surface used in the ankle portion.

The present invention also provides, in a second aspect, a sock suitable for wearing on a leg of a leg ulcer patient, the sock comprising an ankle portion made from material having the ability to apply compression to the ankle area of the patient's foot.

Some, most, substantially all or all of the ankle portion may be made from material having the ability to apply compression to the ankle area of the patient's foot. Preferably, all, or substantially all, of the area that, in use, will be coextensive with the patient's ankle is made from material having the ability to apply compression to the ankle area of the patient's foot, and more preferably all of the gaiter region of the sock is made from material having the ability to apply compression to the ankle area of the patient's foot.

The use of such a material having the ability to apply compression in the sock is advantageous because it allows compression to be applied to the ankle area without restricting the movement of the ankle joint. Conventional compression means tend to either have difficulty applying compression to complex mobile areas such as the ankle region, or are unable to apply compression to such areas without causing a restriction in flexibility. Furthermore, the use of such a material provides additional support to this sensitive area.

Preferably, the material having the ability to apply compression to the ankle area of the patient's foot comprises two or more different fibers, for example, it may be knitted from two or more different fibers. Preferably, the material includes one or more elasticated fibers, for example selected from Lycra™, elastane, Spandex™, Dorlastan™, Spanzelle™, Vyrene™, natural rubber EPDM and polybutadiene.

The Youngs modulus of the elastic fiber is suitably from $10^5$ to $10^7$ Pa, for example, of the order of $10^6$ Pa.

When fibers other than elasticated fibers are included, these may be any fibers suitable for use in a sock and may be natural fibers or synthetic fibers or a combination thereof. Suitably, the material is knitted material and the stitch used for knitting is such that it generates compression. The peaks and valleys, the openness of the stitch and any openings all contribute to the generation of compression and accordingly one or more of these factors can suitably be adjusted to achieve the desired compression.

Preferably, the portions of the sock other than the ankle portion and any cuff portion that is included around the mouth of the sock are made of material that does not have any significant ability to apply compression. The sock should preferably only apply compression in specific zones of its structure. In particular it is preferred that the portions of the sock other than the ankle portion and any cuff portion that is included around the mouth of the sock are made of material that does not include elasticated fibers.

It is preferred that the portions of the sock other than the ankle portion and 5 any cuff portion apply minimal compression, such as less than 10 mmHg, for example, less than 5 mmHg.

There will of course be some pressure variation depending on how large the leg is on which the sock is worn. However the sock is designed so as to fit specific leg size ranges. Accordingly, the portions of the sock other than the ankle portion and any cuff portion suitably apply minimal compression, such as less than 10 mmHg, for example, less than 5 mmHg, when worn on a leg within the size range specified for the sock.

Suitably the portions of the sock other than the ankle portion and any cuff portion are knitted with an open stitch in order to generate minimal compression.

When considering the pressure applied to the sock, for example, from a compression applying means, such as bandages, compression stockings, LaPlace's Law applies. Therefore, the pressure applied is inversely proportional to the radius, and pressure is higher along the shinbone. This is minimized by keeping the pressure applied by the sock as low as possible, without them falling down, in particular by having the portions of the sock other than the ankle portion and any cuff portion suitably apply minimal compression, such as less than 10 mmHg, for example, less than 5 mmHg.

When the sock it used in combination with a compression sleeve it is preferred that the sock has no significant ability to apply compression in any region. This means that the only compression applied to the limb from the combination of sock and sleeve is that applied by the compression sleeve, and this allows greater control of the treatment delivered to the patient by the medical practitioner.

The use of padding in the sock in the areas that in use cover the ankle and shin is advantageous because, when used in conjunction with compression applying means such as bandages, compression stockings, compression sleeves or air bladders, it provides cushioning for these bony prominences and in particular reduces the high pressures that can otherwise occur along bony prominences when compression is applied.

Suitably, the padding may be provided by the provision of a thicker layer of material than is used in the surrounding region. For example, in an embodiment whereby the sock is knitted, areas of thicker knitting may be used in the areas of the ankle portion and leg portion that, in use, will cover the ankle and the shin, than is used in the surrounding region.

The padding may suitably be provided by the use of loops, such as terry loops, in the areas of the ankle portion and the leg portion that, in use, will be over the ankle and the shin, on the side that in use will be on the inner surface of the sock, adjacent the skin. Terry loops are of course well known in the art, for example, on towels and on athletic socks under the heel for long-distance use, and may be formed when the ground structure is knitted on alternate needles with the remaining needles being overlapped by the back guide which causes the formation of yarn loops that are proud of the fabric ground structure. The terry loops may be sized as desired to provide the required degree of padding, for example extra large terry loops may be used, with larger loops providing more padding.

The padding over the ankle may be material that is 1 mm thick or more, preferably 1.5 mm thick or more, for example, up to 2 mm thick.

The padding over the shin may be material that is 2 mm thick or more, preferably 3 mm thick or more, more preferably 4 mm thick or more, for example, up to 5 mm thick.

Preferably, a sock is provided that is in accordance with two or more of the above aspects of the present invention.

The sock may suitably be a knitted sock. The sock may be knitted from any suitable fiber or combination of fibers, provided that they fulfill the requirements as set out above.

Fibers such as wool, cotton, viscose, Lyocel™/Tencel™, nylon, polyester and silk may suitably be used in the sock of the present invention and in particular are suitable for use as base fibers that form the majority of the sock. Fibers such as wool, cotton, viscose, Lyocel™/Tencel™ and silk may also be used in the sock as absorbent fibers.

Fibers such as Coolmax™, Duraspun™, Isolfil™, polypropylene, polyester microfiber, Soft Touch™ P180W and Galaxy™ may suitably be used in the sock of the present invention and in particular are suitable for use as wicking fibers. Fibers such as elastane, Spandex™, Dorlastan™, Spanzelle~M, Vyrene™, Lycra™, natural rubber EPDM and polybutadiene may suitably be used in the sock of the present invention and in particular are suitable for use as elasticated fibers.

Antimicrobial fibers, such as Outlast™, X-Static™ and Amicor™ may suitably be used in the sock of the present invention.

The sock may suitably be knitted from a combination of fibers including one or more fine natural fibers, in particular first spin wool, merino wool and silk threads, to increase the comfort of the sock on the patient's foot. The use of one or more of these fibers also assists in temperature and moisture control at the foot.

The sock may suitably be knitted from a combination of fibers including one or more antimicrobial fibers, such as silver fibers.

Preferably, the sock comprises a foot portion having a closed toe. This is preferable as it avoids discomfort to the patient due to the toes of his foot becoming cold.

The sock preferably comprises a leg portion that, in use, extends upwardly from the foot to cover some, most, substantially all, or all, of the calf of the patient. Suitably, the leg portion in use extends upwardly from the foot to cover all of the calf of the patient. Preferably, the leg portion of the sock terminates at or around, or just below, the knee of the patient, and therefore the sock is preferably a knee-high sock.

Preferably, the sock comprises an elasticated cuff portion around the mouth of the sock. The cuff portion is preferably a double cuff portion in order to increase the ability of the sock to stay up.

The cuff portion may suitably be 1 mm thick or more, and preferably is from 1 mm to 5 mm thick, for example, 4.5 mm thick. The cuff portion preferably has seams on the side that, in use, is on the outer surface of the sock, in order to avoid rubbing against the skin and the formation of blisters.

Preferably, the foot portion is made of material that is of lower friction on the side that in use is on the outer surface of the sock than on the side that in use is on the inner surface of the sock. In one embodiment, the entire sock may be made of material that is of lower friction on the side that in use is on the outer surface of the sock than on the side that in use is on the inner surface of the sock. Accordingly, the design allows for the inner part of the sock to have a higher coefficient of friction than the outside. This is beneficial because it allows any compression applying means worn with the sock to slip against the outside of the sock without causing the inside of the sock to rub against the skin, causing blisters to form or causing a non-occlusive dressing applied to the wound to tuck up at the edges.

The sock suitably comprises a foot portion having the seams on the side that, in use, is on the outer surface of the sock. This is beneficial as it avoids rubbing against the skin and the formation of blisters. It is also preferable that the sock comprises a foot portion that has a thin profile, as this allows the patient's normal footwear to be worn with the sock, even while the sock is also worn with compression applying means. Preferably, the sock comprises a foot portion that is less than 2 mm thick, more preferably less than 1 mm thick, for example, 0.75 mm thick or less.

The sock of the present invention suitably comprises an elasticated ankle portion. For example, the ankle portion may be made of a material including one or more elasticated yarns, for example, Lycra™ This allows the sock to be put on and taken off more easily, and also permits flexion of the ankle.

Preferably, the sock is padded around the ankle portion. For example, the ankle portion may, on the side that in use is on the inner surface of the sock, have terry loops. Such loops may suitably be provided so as to be, in use, in a circular pattern around the ankle. The use of such padding provides support for the sensitive area around the ankle. The ankle portion may be made of material that is 1 mm thick or more, for example 1.5 mm or more; suitably the ankle portion is made of material that is from 1 mm to 5 mm thick.

In one embodiment the sock itself includes an indication of the leg/foot size range for which it is intended, for example, the sock may include a label that indicates the leg/foot size range for which it is intended. Alternatively, or additionally, the sock may be sold in a package that indicates the leg/foot size range for which it is intended.

The sock can be worn on its own or can be worn with compression applying means such as bandages, compression stockings, compression sleeves or air bladders.

The socks may be handed, with one sock being a left foot sock and one sock being a right foot sock.

The invention further provides a kit comprising one or more socks in accordance with any one or any combination of two or more of aspects above, together with one or more compression applying means, such as bandages, compression stockings, compression sleeves, and air bladders.

In one embodiment of this aspect, the sock comprises ventilation channels and the compression applying means comprises evaporation channels that, in use, correspond with the ventilation channels in the sock so as to allow water vapor to diffuse along the ventilation channels and then to be released to the atmosphere from the evaporation channels.

BRIEF DESCRIPTION OF THE DRAWINGS

An embodiment of the present invention will now be further described, by means of example only, with reference to the drawings, in which.

DETAILED DESCRIPTION OF THE PREFERRED EMBODIMENTS

Figure 1:
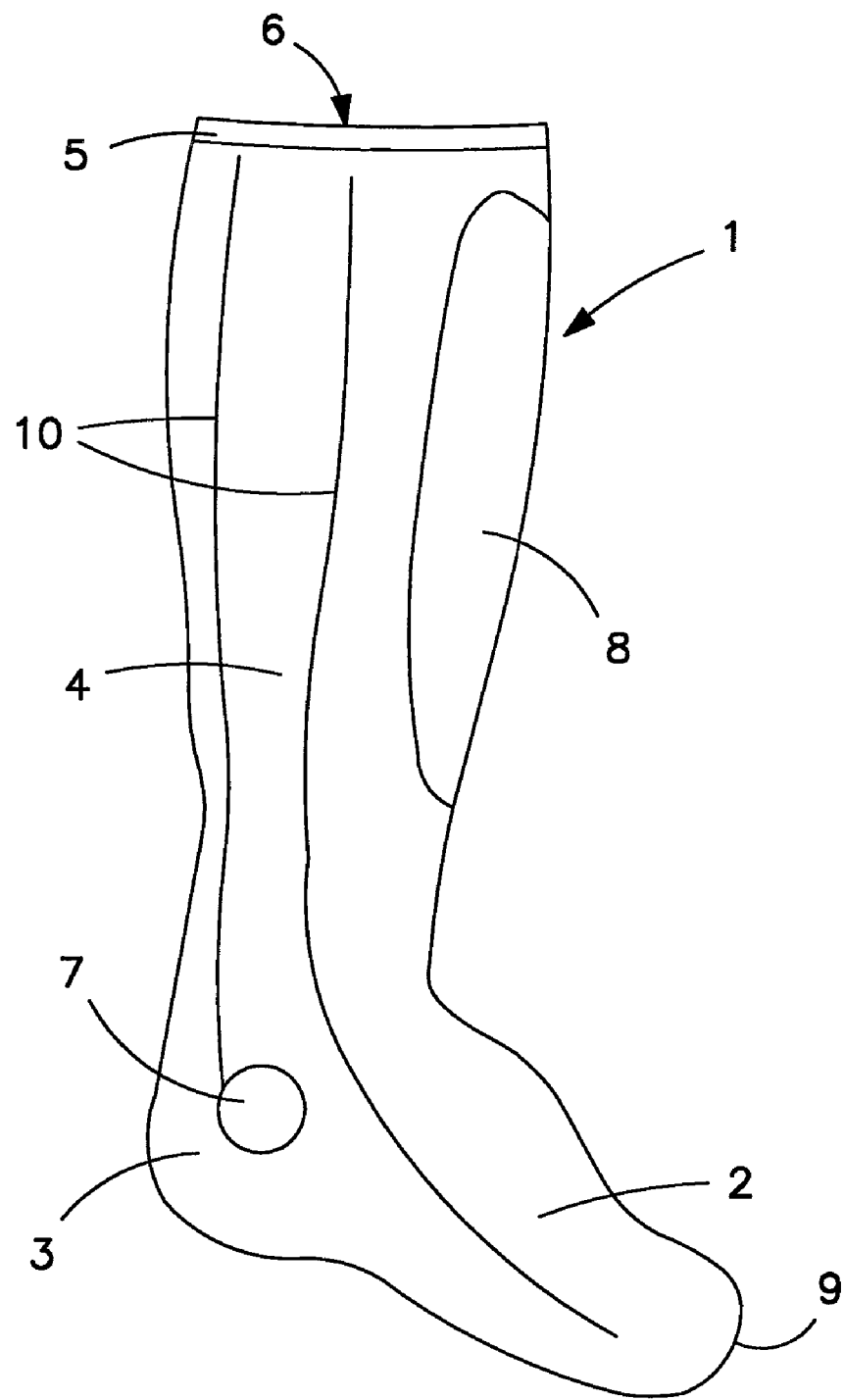
FIG. 1 is a diagram of a sock in accordance with the present invention.

The sock 1 shown in FIG. 1 is shaped so as to fit on the foot and calf of a leg ulcer patient and comprises a foot portion 2 and an ankle portion 3 leading to a leg portion 4. A cuff portion 5 is provided at the top of the leg portion 4, around the mouth 6 of the sock 1.

The sock 1 is a knee-high sock, with leg portion 4 in use extending upwardly from the foot of the patient to cover all of the calf of the patient and terminating at the cuff portion 5 at or around the knee of the patient.

The ankle portion 3 is knitted from a combination of cotton and/or wool together with the wicking fiber Coolmax™, antibacterial silver fibers and the elasticated fiber Lycra™. This portion of the sock applies compression of about up to 70 mm Hg.

The foot portion 2 and the leg portion 4 are knitted with an open stitch from a combination of cotton and/or wool together with the wicking fiber Coolmax™ and antibacterial silver fibers. These portions of the sock apply minimal compression, of less than 5 mmHg.

The ankle portion 3 includes padding 7 by the use of extra large terry loops in the area that, in use, will be over the ankle, on the side that in use will be on the inner surface of the sock, adjacent the skin. The padding 7 by the ankle is about 1.5 mm thick.

The leg portion 4 includes padding 8 by the use of extra large terry loops in the area that, in use, will be over the shin, on the side that in use will be on the inner surface of the sock, adjacent the skin. The padding 8 by the shin is about 4 mm thick.

The foot portion 2 has a closed toe 9 and has seams on the side that, in use, is on the outer surface of the sock 1. The foot portion 2 has a thin profile, of about 0.75 mm thick.

The sock 1 comprises ventilation channels 10 of ribbed construction provided both in the foot portion 2 and in the leg portion 4. The ventilation channels 10 run away from the ankle portion 3, and water vapor may be transferred laterally by diffusion along these channels 10.

The cuff portion 5 is elasticated and is about 1.5 mm thick. The cuff portion 5 is a double cuff portion and comprises synthetic rubber pieces. The seams of the cuff portion 5 are provided on the side that, in use, is on the outer surface of the sock 1.

The sock 1 includes a label (not shown) on its inner surface, which label indicates the size of leg on which the sock is to be worn in order to generate the desired pressure.

The sock 1 can suitably be worn on the foot and calf of a leg ulcer patient, over any dressings positioned on the wound. The sock 1 allows moisture to be distributed away from the skin and into the atmosphere. Further, when used with a compression applying means, for example bandages or a compression sleeve, the padding 7, 8 in the sock 1 prevents high pressures being applied to the bony areas of the ankle and the shin.

Figure 2:
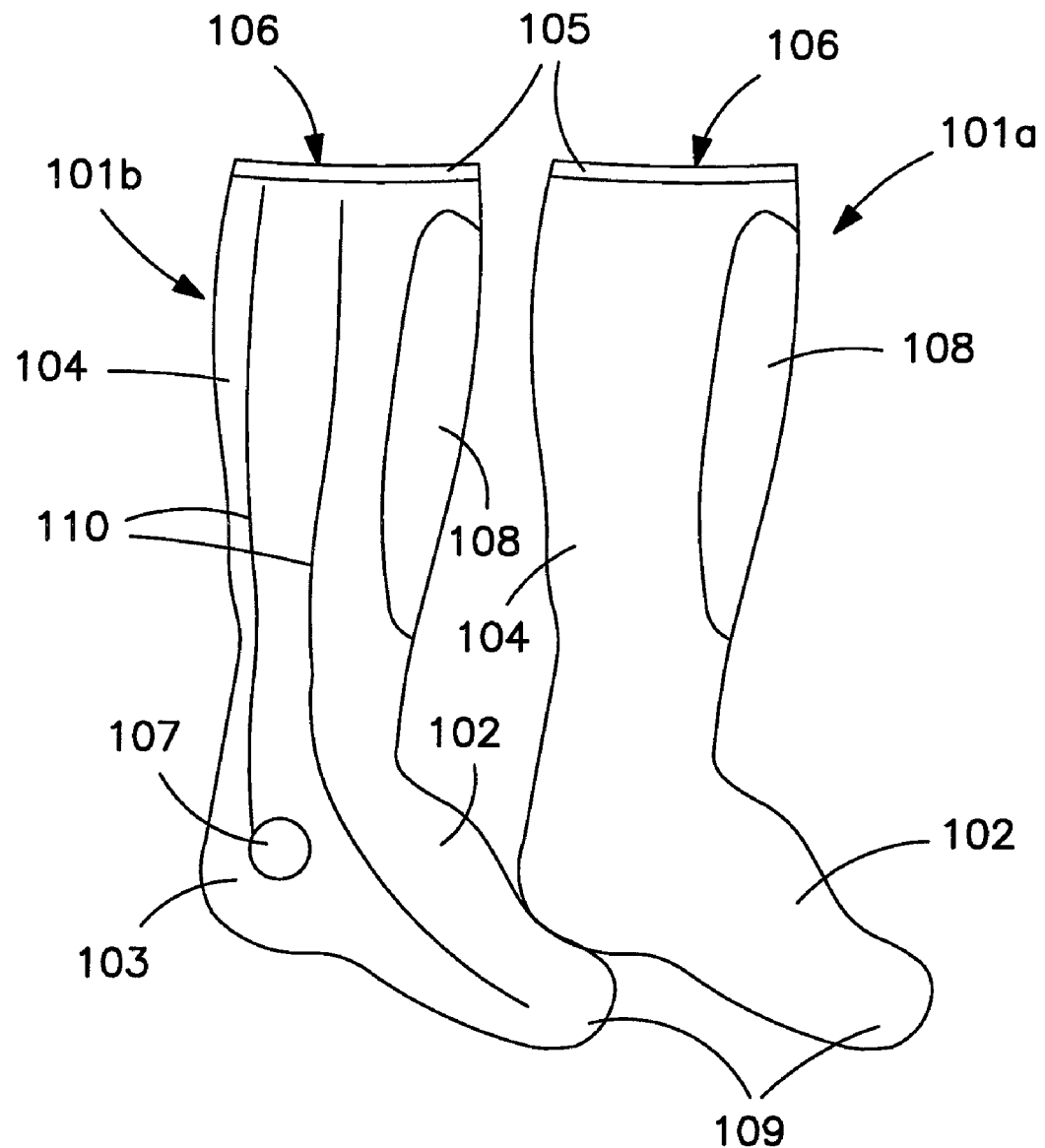
FIG. 2 is a diagram of a pair of socks in accordance with the present invention.

FIG. 2 shows a pair of socks 100 which comprises a left sock 101a and a right sock 101b. Each of the socks 101a, 101b, is as sock 1 shown in FIG. 1 and described above. In FIG. 2, a reference number 100 greater than a reference number in FIG. 1 indicates a like part; for example in FIG. 2 reference number 103 indicates an ankle portion corresponding to ankle portion 3 shown in FIG. 1 and described above.

Figure 3:
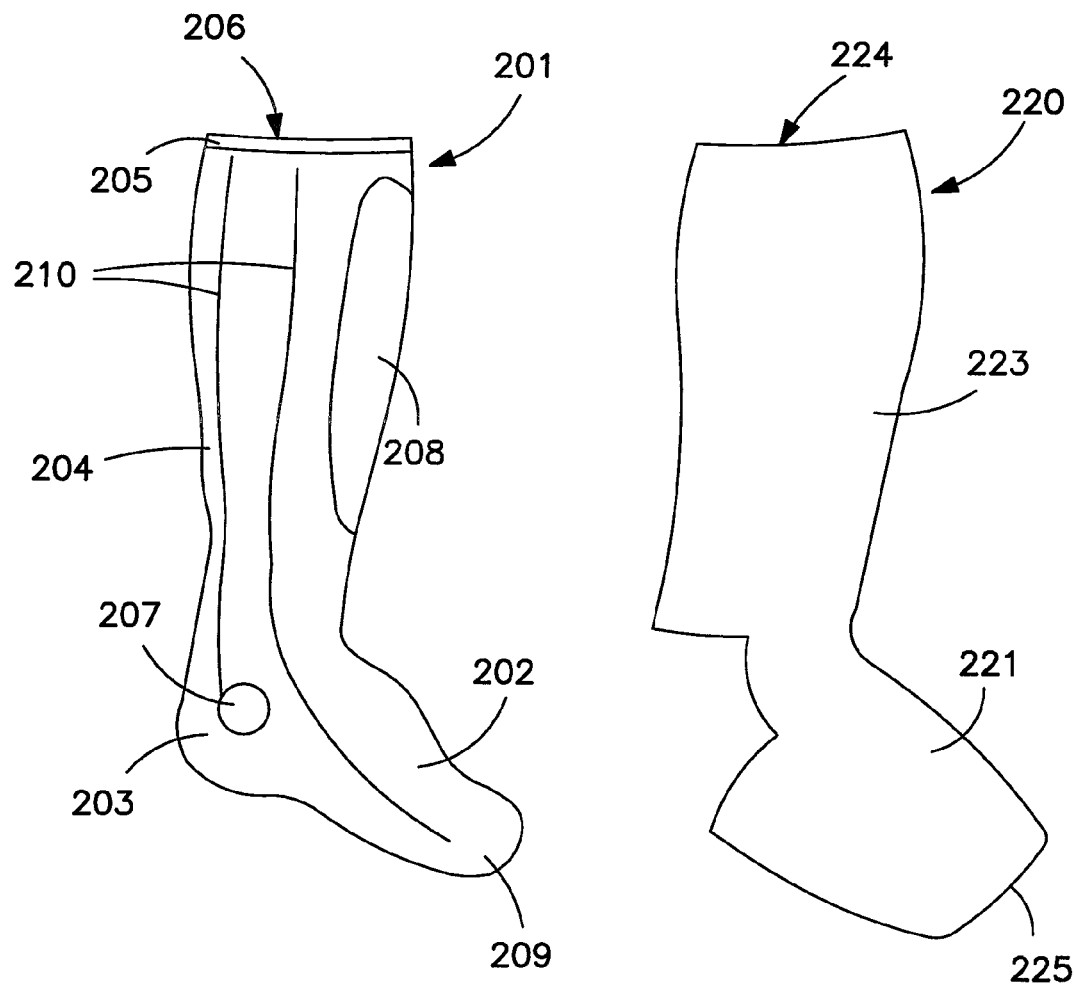
FIG. 3 is a diagram of a kit including a sock in accordance with the present invention.

FIG. 3 shows a kit 200 which comprises a sock 201 and a compression sleeve 220. The sock 201 is as sock 1 shown in FIG. 1 and described above. In FIG. 3, a reference number 200 greater than a reference number in FIG. 1 indicates a like part; for example in FIG. 3 reference number 203 indicates an ankle portion corresponding to ankle portion 3 shown in FIG. 1 and described above.

The compression sleeve 220 is shaped so as to fit on the foot and calf of a leg ulcer patient, over the sock 201, and comprises a foot portion 221 and a leg 10 portion 223.

The compression sleeve 220 is knee-high, with leg portion 223 in use extending upwardly from the foot of the patient to cover all of the calf of the patient and terminating at mouth 224 at or around the knee of the patient, at or slightly above the height of the sock 201.

The compression sleeve 220 is provided with inflatable and deflatable bladders (not shown) which are used to apply compression to the leg of the leg ulcer patient.

The foot portion 221 of the compression sleeve 220 has an open toe 225.

The compression sleeve 220 comprises evaporation channels (not shown) that, in use, correspond with the ventilation channels 210 in the sock 201. Accordingly, water vapor can diffuse along the ventilation channels 210 and then be released to the atmosphere from the evaporation channels.

The sock 201 can suitably be worn on the foot and calf of a leg ulcer patient, over any dressings positioned on the wound, with the compression sleeve 220 being worn over the sock 201. The sock 201 allows moisture to be distributed away from the skin and into the atmosphere. Further, when used with a compression applying means, the padding in the sock 201 prevents high pressures being applied to the bony areas of the ankle and the shin. The compression sleeve applies pressure as required to the foot and calf of the patient. The sock 201 preferably applies no compression to the limb and is uniformly knitted from a mixture of textile fibers such as cotton and a wicking fiber. In this way moisture can be wicked from the whole of the skin surface under the compression sleeve and is allowed to evaporate from those areas of the sock not covered by the compression sleeve.

Embodiments of the present invention will now be further described, by means of the following example.

Example 1

Socks made from various yarn blends were tested over forty wash cycles to determine those blends with the best wicking properties.

| Sample No | Yarn blend (Nm count system) |
|---|---|
| 1 | ¹⁄₄₀ cotton × ¹⁄₅₀ Coolmax/Coolmax antibacterial |
| 2 | ¹⁄₄₀ cotton × ¹⁄₅₀ polypropylene |

The socks were subjected to lateral wicking tests performed on the rear calf section running down the length of the sock. The wicking results reflect lateral movement of moisture along the length of the sock.

The test was performed as follows: Cut a test sample of size: 15 mm×100 mm using a pair of scissors. Mark a line 10 mm parallel to the bottom 15 mm edge on each of the samples.

Set up two stands and clamps and attach a single metal rod to the clamps on each stand. Ensure that the rod is horizontal. Attach three bulldog clips to the metal rod, such that each clip is approximately 10 mm apart.

Place the labjack below the metal rod with the clamps on either side.

Place 10 ml of eosin dye into each of the three adjacent chambers of a culture tray. Place the tray onto the labjack. Clip each unmarked 15 mm end of the samples to the bulldog clips, ensuring that samples are vertically and horizontally straight and are directly above the chambers containing the eosin dye. Increase the labjack height until the level of the dye reaches the marked line (sample end submerged to the 10 mm line).

Immediately start the stop clock. After 60 seconds, lower the labjack, remove the test samples carefully and measure the furthest wicking distance in mm from the marked line.

| | Wick Distance (mm) | | | | | |
|---|---|---|---|---|---|---|
| No. | Un-washed | 1 wash | 5 washes | 15 washes | 30 washes | 40 washes |
| 1 | 23 | 26 | 53 | 60 | 65 | 62 |
| 2 | 50 | 28 | 35 | 51 | 57 | 59 |

We claim:

1. A compression therapy kit comprising a sock suitable for wearing on a limb of a patient, the sock comprising material having the ability to wick moisture away from the skin surface and the sock comprising padding located in those areas of the sock which in use will cover the ankle and shin of the patient, and one or more compression applying sleeves with inflatable bladders which in use apply compression over the sock to the ankle and shin of the patient.

2. The kit according to claim 1, wherein the sock and compression applying sleeves are applied separately and sequentially to the leg of the patient.

3. The kit according to claim 1, wherein the sock comprises one or more wicking fibers on the side of the sock that in use is in contact with the patient's skin and includes absorbent material on the side of the sock that in use is on the outer surface of the sock.

4. The kit according to claim 1, wherein a foot portion of the sock is of lower friction on the side of the sock that in use is on the outer surface of the sock than on the side that in use is on the inner surface of the sock.

5. A method for the treatment of venous leg ulcers, deep vein thrombosis (DVT), vascular disorders or the reduction of oedema comprising applying the sock and the one or more compression applying sleeves with inflatable bladders of the kit of claim 1 separately and sequentially to the leg of a patient.

* * * * *